United States Patent
Samuelsson et al.

(10) Patent No.: US 7,867,208 B2
(45) Date of Patent: Jan. 11, 2011

(54) ABSORBENT ARTICLE HAVING DISPOSAL FASTENING MEANS

(75) Inventors: Ann Samuelsson, Lindome (SE); At J. Plasman, AC Roden (NL); Pontus Winqvist, Stora Höga (SE); Ingemar Fernfors, Mölndal (SE); Anna-Gerd Doverbo, Mölndal (SE)

(73) Assignee: SCA Hygiene Products AB, Gothenburg (SE)

( * ) Notice: Subject to any disclaimer, the term of this patent is extended or adjusted under 35 U.S.C. 154(b) by 0 days.

(21) Appl. No.: 11/998,422

(22) Filed: Nov. 30, 2007

(65) Prior Publication Data

US 2008/0103470 A1 May 1, 2008

Related U.S. Application Data

(63) Continuation of application No. PCT/SE2005/000821, filed on Jun. 1, 2005.

(51) Int. Cl.
*A61F 13/15* (2006.01)
*A61F 13/20* (2006.01)
(52) U.S. Cl. .............................. 604/385.13; 604/385.11
(58) Field of Classification Search ............ 604/385.01, 604/385.13, 385.11
See application file for complete search history.

(56) References Cited

U.S. PATENT DOCUMENTS

| | | | | |
|---|---|---|---|---|
| 3,931,666 | A | * | 1/1976 | Karami ..................... 24/304 |
| 4,923,455 | A | * | 5/1990 | Dean et al. ............. 604/385.13 |
| 5,037,414 | A | * | 8/1991 | Booth ................... 604/385.13 |
| 5,575,784 | A |   | 11/1996 | Ames-Ooten et al. |
| 6,454,748 | B1 |   | 9/2002 | Ives |
| 2002/0065500 | A1 |   | 5/2002 | Rossi |
| 2003/0153891 | A1 | * | 8/2003 | Molee ................... 604/385.13 |
| 2007/0149942 | A1 | * | 6/2007 | Arco et al. ............. 604/385.13 |

FOREIGN PATENT DOCUMENTS

| | | |
|---|---|---|
| EP | 0 623 330 A2 | 11/1994 |
| EP | 0 732 094 A2 | 9/1996 |
| EP | 0 888 766 A1 | 1/1999 |
| EP | 0 890 351 A2 | 1/1999 |
| EP | 1 121 917 A2 | 8/2001 |
| JP | 10-151153 A | 6/1998 |
| JP | 2002-45401 A | 2/2002 |
| RU | 2 089 081 | 9/1997 |
| RU | 2 269 328 | 2/2006 |
| WO | WO 92/10957 | 7/1992 |
| WO | WO 02/056814 | 7/2002 |
| WO | WO 2006/071144 A1 | 7/2006 |

* cited by examiner

*Primary Examiner*—Michele Kidwell
(74) *Attorney, Agent, or Firm*—Buchanan Ingersoll & Rooney PC

(57) ABSTRACT

An absorbent article (10) includes an absorbent core (12) disposed between an inner coversheet (14) and an outer coversheet (16). The article further includes at least one disposal fastener (18) which is directly or indirectly joined to the outer coversheet (16). The disposal fastener (18) includes a fastening element (20) which allows the article to be secured in a configuration that provides a convenient disposal after the article has been used. The disposal fastener (18) is covered by a material layer (22) having a surface area such that it extends beyond the disposal fastener (18). The material layer (22) is attached to or forms an integral part of the outer coversheet (16) so as to keep the disposal fastener (18) hidden when not in use. The material layer (22) is releasable from the outer coversheet (16) so as to expose the disposal fastener (18) for use.

25 Claims, 8 Drawing Sheets

ABSORBENT ARTICLE HAVING DISPOSAL FASTENING MEANS

CROSS-REFERENCE TO RELATED APPLICATIONS

The present application is a continuation of international application no. PCT/SE2005/000821, filed on Jun. 1, 2005, the entire contents of which is incorporated herein by reference.

TECHNICAL FIELD

The present invention refers to an absorbent article such as a diaper, a pant diaper, a sanitary napkin or incontinence guard, comprising an absorbent core disposed between an inner coversheet and an outer coversheet, said article further comprising at least one disposal fastening means which is directly or indirectly joined to the outer coversheet, said disposal fastening means having a fastening element adapted to fasten to at least a portion of the outer coversheet which allows the article to be secured in a configuration that provides a convenient disposal after said article has been used.

BACKGROUND OF THE INVENTION

After use, absorbent articles are usually folded or rolled up so that the soiled portion is wrapped inside for disposal. In order to prevent the soiled article unfolding and to keep the soiled portion inside, it is desired that a so-called "disposal fastening means" is arranged to keep the article in the folded or rolled-up state under disposal. For a diaper having fastening means in the form of adhesive tape tabs or hook-and-loop type fasteners for fastening the diaper about the waist of the wearer, this fastening means may also be used as the disposal fastening means. However, other articles, particularly pant diapers, require special disposal fastening means, usually comprising a fastening element, for example an adhesive or a mechanical fastening element, which is fixed at one end to the front or rear of the article and folded up, so that in normal use the adhesive or the mechanical fastening element is brought in an unexposed position. The strip may be unfolded so as to expose the fastening element when it is desired to use it as a disposal fastening means.

EP-A-1 121 917 discloses a pant diaper having a disposal fastening means in the form of tape strips arranged in the vicinity of the side edges of the diaper. Each tape strip comprises two portions, a first portion extending longitudinally in parallel to the side edges and a second portion extending from a predetermined region of the first portion longitudinally or transversely of the diaper. The disposal fastening means is said to be adapted to hold the diaper in its rolled up state for disposal without leakage through the waist- or leg-openings.

International patent application PCT/SE2004/002026 discloses a pant-type absorbent article comprising at least one fastening means disposed in the side joint region between the joined side edges of the article. Upon tearing the side joint region, the fastening means is exposed.

US 2003/0153891 discloses an absorbent article having a disposal fastening means, said disposal fastening means including visible indicia. These indicia make it easier to locate the disposal fastening means, and may provide instructions to a user or caregiver.

US 2002/0065500 describes a plastic bag used for disposal of diapers which is located directly on the diaper and contained within a tearable enclosure on the diaper. When disposal of the diaper is required, the enclosure is torn open, the plastic bag pulled out and the soiled diaper inserted into the plastic bag.

EP 0 623 330 discloses a shorts-type diaper provided with a tape fastener intended to fasten the used diaper when discarding. EP00732094 discloses a similar article, in which the tape fastener is elastic.

JP 2002 045401 teaches a method of fixing a folded disposal tape to the backsheet of a diaper, using an adhesion layer to keep the tape folded while the article is being worn.

Many of these known disposal fastening means may be opened and even removed by mistake by the wearer or caregiver before the article is removed for disposal. This is particularly a problem for babies, who can remove a disposal fastening means attached to their diaper, thus making it ineffective as a fastening means. The disposal fastening means may also be opened under movements between a diaper and surrounding clothing and can then stick to the clothing. Untimely opening or removal of the disposal fastening means can lead to it becoming dirty or damaged, thus reducing its fastening ability.

OBJECT AND SUMMARY

One object of the disclosure is to provide an absorbent article having a disposal fastening means that reduces the risk of being opened by mistake before the article is ready for disposal. It is of particular interest to provide a disposal fastening means which draws less attention and is more discrete, so that babies show less interest in it. It is desirable to provide a disposal fastening means which is concealed and not immediately accessible, thus minimizing the risk of undesirable opening or removal.

An absorbent article of the type mentioned above has a disposal fastening means that is covered by a material layer. This material layer has a surface area such that it extends beyond the disposal fastening means, and is attached to or forms an integral part of the outer coversheet so as to keep the disposal fastening means hidden when not in use. The material layer is releasable from the outer coversheet so as to expose the disposal fastening means for use.

According to one aspect, the material layer is provided with perforations, breakable seals or the like for releasing it from the rest of the outer coversheet and thus exposing the disposal fastening means.

In another embodiment, the outer coversheet is a laminate comprising a garment facing layer and at least one additional layer located on the inside of the garment facing layer. In this embodiment, the material layer may be an integral part of the garment facing layer of the outer coversheet, and the garment facing layer may be perforated around at least a part of the circumference of the material layer.

According to a further embodiment, the material layer is separate piece of material which is joined to the outer coversheet by a breakable seal. The breakable seal may comprise welds, glue sites, etc. which join the material layer to the outer coversheet.

In a preferred embodiment, the material layer is of a composition and structure such that it closely resembles the garment-facing surface of the outer coversheet, especially a nonwoven material or plastic film. Furthermore, the outer coversheet according to the invention may comprise nonwoven material in at least the garment-facing surface thereof.

The fastening element of the disposal fastening means may be a hook portion of a hook-and-loop type fastener, or alternatively an adhesive tape tab. In one embodiment, the disposal fastening means is folded under the material layer.

The disposal fastening means may be joined to the material layer. Alternatively, the material layer is an integral part of the outer surface of the disposal fastening means.

In a preferred embodiment, the disposal fastening means comprises an elastic material such that—when not under tension—the disposal fastening means lies hidden under the material layer but can be extended under tension.

The disposal fastening means is of particular interest when the article is a pant-type absorbent article. This is because such articles do not have side-fastening tape tabs, which are otherwise used to keep the rolled-up article in a packaged state for disposal. The disposal fastening means is preferably located on the front or back portions of such a pant diaper. Desirably, a pattern is printed on the garment facing surface of the outer coversheet and at least a part of the pattern is located on the material layer.

DEFINITIONS

Absorbent Article and Pant Type Absorbent Article

The term "absorbent article" refers to products that are placed against the skin of the wearer to absorb and contain body exudates, like urine, feces and menstrual fluid. The disclosure mainly refers to disposable absorbent articles, which means articles that are not intended to be laundered or otherwise restored or reused as absorbent articles after use. The disclosure is particularly of relevance to pant-type absorbent articles, which have a defined waist opening and a pair of leg openings and which are pulled onto the body of the wearer by inserting the legs into the leg openings and pulling the article up over the waist. Examples of such pant-type absorbent articles are pant diapers, sanitary pants and incontinence pants worn by incontinent adults. Pant-type absorbent articles usually comprise a front portion, a crotch portion and a back portion, said front and back portions being joined to each other along two opposite longitudinal side edges to define a waist-opening and a pair of leg-openings.

Inner Coversheet

The term "inner coversheet" refers to the liquid permeable material sheet forming the inner cover of the absorbent article and which in use is placed in direct contact with the skin of the wearer. The inner coversheet can comprise a nonwoven material, e.g. spunbond, meltblown, carded, hydroentangled, wet-laid etc. Suitable nonwoven materials can be composed of natural fibers, such as woodpulp or cotton fibres, man-made fibres, such as polyester, polyethylene, polypropylene, viscose, rayon etc. or from a mixture of natural and man-made fibres. The inner coversheet material may further be composed of tow fibres, which may be bonded to each other in a bonding pattern, as e.g. disclosed in EP-A-1 035 818. Further examples of inner coversheet materials are porous foams, apertured plastic films etc. The materials suited as inner coversheet materials should be soft and non-irritating to the skin and be readily penetrated by body fluid, e.g. urine or menstrual fluid. The inner coversheet may further be different in different parts of the absorbent article.

Outer Coversheet

The outer coversheet refers to the liquid impervious material forming the outer cover of the absorbent article. The outer coversheet can comprise a thin plastic film, e.g. a polyethylene or polypropylene film, a nonwoven material coated with a liquid impervious material, a hydrophobic nonwoven material, which resists liquid penetration, or a laminate of a plastic film and a nonwoven material. The outer coversheet material may be breathable so as to allow vapour to escape from the absorbent core, while still preventing liquids from passing therethrough. Examples of breathable outer coversheet materials are porous polymeric films, nonwoven laminates of spunbond and meltblown layers and laminates of porous polymeric films and nonwoven materials. Preferably, the outer coversheet comprises nonwoven material in at least the garment-facing surface thereof.

Absorbent Core

The "absorbent core" is the absorbent structure disposed between the two coversheets of the absorbent article. The absorbent core can be of any conventional kind. Examples of commonly occurring absorbent materials are cellulosic fluff pulp, tissue layers, highly absorbent polymers (so called superabsorbents), absorbent foam materials, absorbent nonwoven materials or the like. It is common to combine cellulosic fluff pulp with superabsorbent polymers in an absorbent core. Superabsorbent polymers are water-swellable, water-insoluble organic or inorganic materials capable of absorbing at least about 20 times their own weight of an aqueous solution containing 0.9 weight percent of sodium chloride. Organic materials suitable for use as superabsorbent materials can include natural materials such as polysaccharides, polypeptides and the like, as well as synthetic materials such as synthetic hydrogel polymers. Such hydrogel polymers include, for example, alkali metal salts of polyacrylic acids, polyacrylamides, polyvinyl alcohol, polyacrylates, polyacrylamides, polyvinyl pyridines, and the like. Other suitable polymers include hydrolyzed acrylonitrile grafted starch, acrylic acid grafted starch, and isobutylene maleic anhydride copolymers and mixtures thereof. The hydrogel polymers are preferably lightly cross-linked to render the material substantially water insoluble. Preferred superabsorbent materials are further surface cross-linked so that the outer surface or shell of the superabsorbent particle, fibre, flake, sphere, etc. possesses a higher crosslink density than the inner portion of the superabsorbent. The superabsorbent materials may be in any form which is suitable for use in absorbent composites including particles, fibres, flakes, spheres, and the like.

A high liquid storage capacity is provided by the use of high amounts of superabsorbent material. For an absorbent core comprising a matrix of hydrophilic fibres, such as cellulosic fibres, and superabsorbent material, the proportion of superabsorbent material is preferably between 10 and 90% by weight, more preferably between 30 and 70% by weight.

It is conventional for absorbent articles to have absorbent cores comprising layers of different properties with respect to liquid receiving capacity, liquid distribution capacity and storage capacity. The thin absorbent bodies, which are common in for example baby diapers and incontinence guards, often comprise a compressed, mixed or layered structure of cellulosic fluff pulp and superabsorbent polymers. The size and absorbent capacity of the absorbent core may be varied to suit different uses, such as infants or adult incontinent persons.

The absorbent core may further include an acquisition distribution layer placed on top of the primary absorbent body, which is adapted to quickly receive and temporarily store discharged liquid before it is absorbed by the primary absorbent core. Such acquisition distribution layers are well known in the art and may be composed of porous fibrous wadding or foam materials.

Disposal Fastening Means

The terms "disposal fastening means" or "disposal fastener" refer to a fastening means or fastener such as a strip of material which comprises a fastening element such as an adhesive tape or a mechanical fastening means in the form of hook members. The disposal fastening means is arranged such that it can fasten to the outer coversheet to keep the absorbent article in the folded or rolled up state after disposal thereof.

BRIEF DESCRIPTION OF THE FIGURES

The embodiments of the invention will, in the following, be closer described with reference to some embodiments shown in the accompanying drawings.

DESCRIPTION OF PREFERRED EMBODIMENTS

Figure 1:
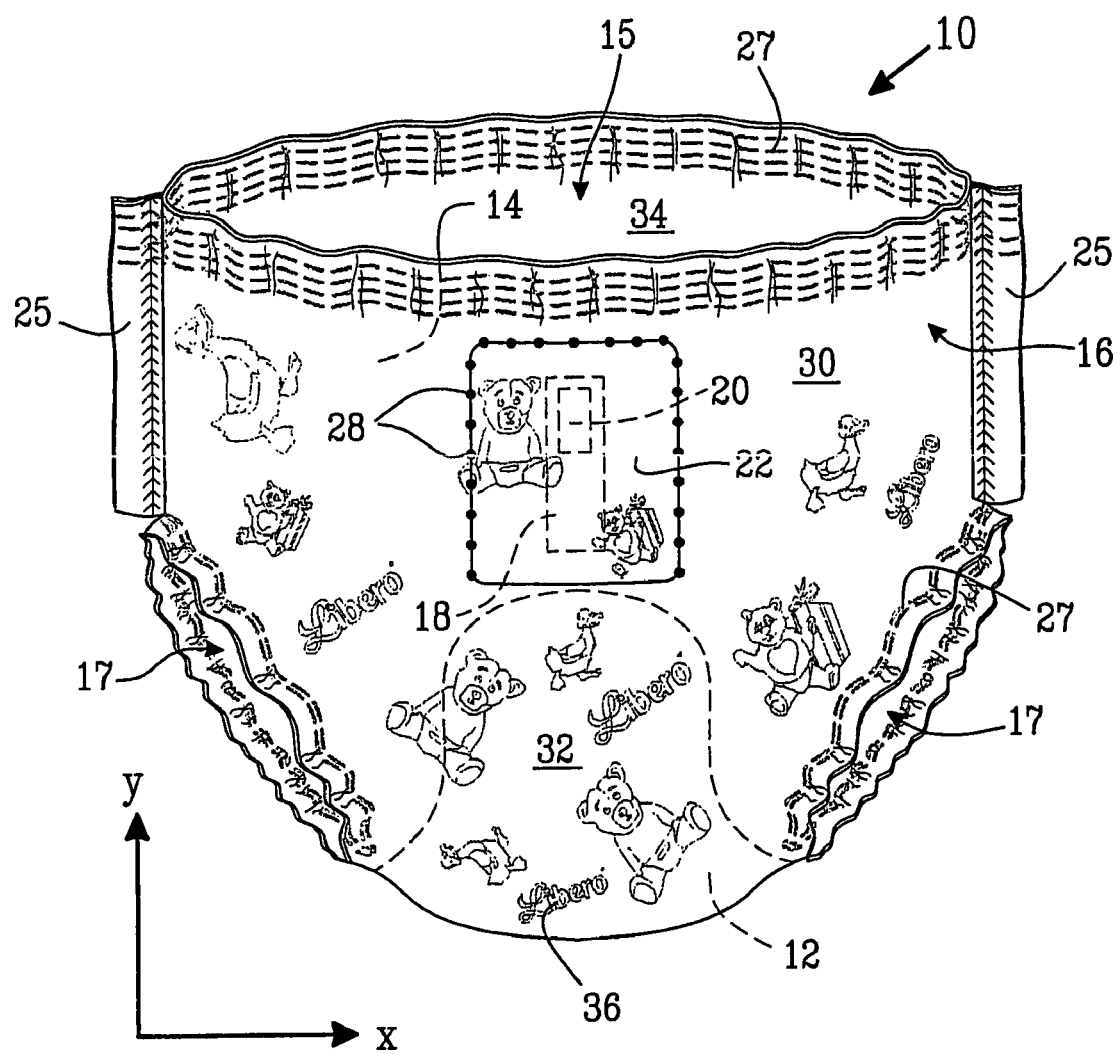
FIG. 1 shows a pant diaper comprising disposal fastening means according to an embodiment of the invention.

As previously mentioned, the absorbent article 10 shown in FIG. 1 (in this case a pant diaper) comprises an absorbent core 12 which is disposed between an inner coversheet 14 and an outer coversheet 16. The disclosure primarily relates to pant type absorbent articles, which have a defined waist opening 15 and a pair of leg openings 17 and which are pulled onto the body of the wearer by inserting the legs into the leg openings and pulling the article up over the waist. Examples of such pant type absorbent articles are pant diapers, sanitary pants and incontinence pants worn by incontinent adults. The pant-type absorbent article comprises a front portion 30, which is the part of the article that in use is intended to extend over the stomach and front hip area of the wearer. The article also comprises a back portion 34, which is the part of the article that in use is intended to extend over the back and the rear hip area of the wearer. The crotch portion 32 of a pant-type absorbent article is the part of the article that in use is intended to extend through the wearer's crotch area, between the legs. The front and back portions 30 and 34 may have different material composition than the crotch portion 32.

The lateral side edges of the front 30 and back 34 portions are joined to each other to form side seams 25, wherein the article assumes a pant-like shape having the aforementioned waist opening and leg openings. The front and back portions are joined along said side seams 25, for example by adhesive, ultrasonic welding, heat sealing or the like. The front and back portions 30 and 34 can either be joined along their side edges with the inner coversheet 14 facing inwards in the side seams 25, as is shown in the drawings. Alternatively they are joined in an overlapping manner, with the inner coversheet 14 of either the front 30 or back 34 portion facing the outer coversheet 16 of the opposite portion.

The waist opening 15 and at least a part of the leg openings 17 are usually elasticized. The elastification is usually accomplished by a plurality of elastic members 27, such as elastic threads, which are contractably affixed between the outer coversheet 16 and the inner coversheet 14. Alternatively elastic materials, such as elastic laminates, may be used to form the front 30 or back 34 portions in those areas where elasticity is desired.

The article further comprises at least one disposal fastening means 18 as described above. The article may, for example, comprise two, three or more disposal fastening means, but in the interests of economy, only one or two disposal fastening means are usually present. The disposal fastening means 18 may be formed from any suitable material. Furthermore, a material layer 22 comprising nonwoven material will be well-concealed against an outer coversheet of nonwoven material, which is the material of choice for the outer coversheet. Typically, the disposal fastening means 18 is located on the front 30 or back 34 portion of the pant diaper.

The disposal fastening means 18 is directly or indirectly attached to the outer coversheet 16, usually via one end of the disposal fastening means 18. By "directly or indirectly" is meant that the disposal fastening means 18 may be attached to the outer coversheet itself, or that one or more layers of material may be present between the disposal fastening means 18 and the outer coversheet 16. Attachment of the disposal fastening means 18 to the outer coversheet 16 may be via glue or welds, but should be sufficiently strong that the disposal fastening means 18 is not easily separated from the article when pulled by hand.

The disposal fastening means 18 has a fastening element 20 adapted to fasten to at least a portion of the outer coversheet 16. The fastening element 20 allows the article to be secured in a configuration that provides a convenient disposal after said article has been used. This may be a rolled-up or folded configuration. The choice of fastening element 20 depends on the nature of the outer coversheet 16—if the outer coversheet 16 is a plastic film, a suitable fastening element 20 will be an adhesive tape tab. If the outer coversheet 16 of the absorbent article 10 is a nonwoven or material layer, a suitable fastening element 20 will be a hook portion of a hook-and-loop type fastener or an adhesive tape tab. The skilled person will understand suitable combinations of fastening element and outer coversheet which will give the required result. The fastening element 20 is normally attached to the disposal fastening means 18 at the end of the disposal fastening means 18 which is furthest from the attachment point of the disposal fastening means to the outer coversheet 16. If the fastening element is an adhesive tape tab, any area with which the adhesive is in contact before use suitably comprises a release-substance, so that the adhesive does not undesirably stick before the disposal fastening means 18 is deployed.

The article has a longitudinal (y) and a transverse direction (x).

The disposal fastening means 18 of the absorbent article 10 is covered by a material layer 22 having a surface area such that it extends beyond the disposal fastening means 18, said material layer 22 being attached to or forming an integral part of the outer coversheet 16 so as to keep the disposal fastening means 18 hidden when not in use, and that said material layer 22 is releasable from the outer coversheet 16 so as to expose the disposal fastening means 18 for use. A more discrete disposal fastening means 18 is provided, so that the chances of babies taking an interest in the disposal fastening means are reduced.

The disposal fastening means 18 is thus hidden by the material layer 22, which provides a uniform, even surface to the article, and reduces the risk of its undesirable opening or removal before the article is ready for disposal. Desirably, the material layer 22 has an appearance which is similar to that of the outer coversheet 16, so that will be well-concealed against the outer coversheet 16. Particularly, the material layer 22 may comprise nonwoven material, which is the material of choice for the outer coversheet 16. In that the disposal fastening means 18 is hidden under the material layer, it makes it more difficult for infants to remove it. Furthermore, the material layer acts to protect the disposal fastening means 18 from dirt and damage.

So that the disposal fastening means 18 is not too difficult to locate, it may be desirable for the material layer 22 to be marked in some way. This may be achieved by introducing a different pattern or colour to its surface from the outer coversheet 16. Alternatively, dashed or continuous lines may be used to indicate the location of the disposal fastening means. However, bright, highly-visible markings or colouring which make the material layer 22 highly attractive to babies should be avoided.

The edges of the material layer 22 which extend beyond the disposal fastening means 18 are attached to, or form an integral part of the outer coversheet 16. This will be described in more detail below.

Suitably, the material layer 22 is provided with perforations, breakable seals or the like for releasing it from the rest of the outer coversheet and thus exposing the disposal fastening means 18.

The material layer 22 may be made from any suitable material, although nonwoven materials are particularly of interest. Suitably, the material layer 22 is of a composition and structure such that it closely resembles the garment-facing surface of the outer coversheet 16, especially a nonwoven material or plastic film. In one embodiment, the material layer 22 can be printed with a pattern 36, e.g. text, logotype, numerals, patterns, cartoon characters or other designs so that it blends in with any such pattern 36 which is printed on the garment facing surface of the outer coversheet 16 (see FIG. 1).

In one embodiment (shown in FIG. 2), the material layer 22 is a separate piece of material which is joined to the outer coversheet 16 by a breakable seal 28, along at least a portion of the circumference of the material layer 22. The breakable seal 28 may comprise welds, glue, etc. which join the material layer to the outer coversheet 16. If the entire circumference of the material layer 22 is joined to the outer coversheet 16 by the breakable seal 28, the material layer 22 will be completely removed upon use. Preferably a part of the circumference of the material layer 22 is not joined to the outer coversheet 16 so as to leave place for a finger to be inserted under the material layer 22 and release it from the outer coversheet 16.

The glue which joins the material layer 22 to the outer coversheet may comprise capsules of fragrance which break when the seal is broken. A pleasant smell is thereby released which covers any offensive smells emitted from the absorbent article.

The disposal fastening means 18 may be joined to the material layer 22 by any suitable means. Alternatively, the material layer 22 is an integral part of the outer surface of the disposal fastening means 18. Alternatively, the disposal fastening means 18 is not joined to the material layer 22 and functions independently of it.

Figure 2:
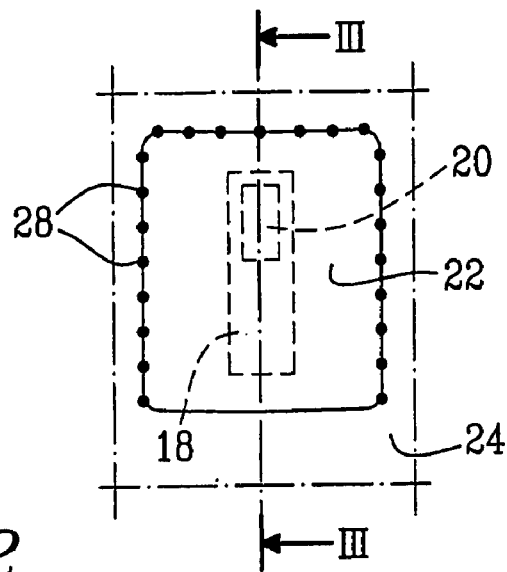
FIG. 2 shows one embodiment of the disposal fastening means according to the invention in which the material layer is attached to the outer coversheet.

FIG. 2 is an enlargement of one embodiment of the disposal fastening means 18 according to the invention in which the material layer 22 is attached to the outer coversheet 16. The material layer 22 is thus a separate piece of material which is fastened to the outer coversheet 16 and held in place by a breakable seal 28 (e.g. welds or glue sites).

Figure 3A:
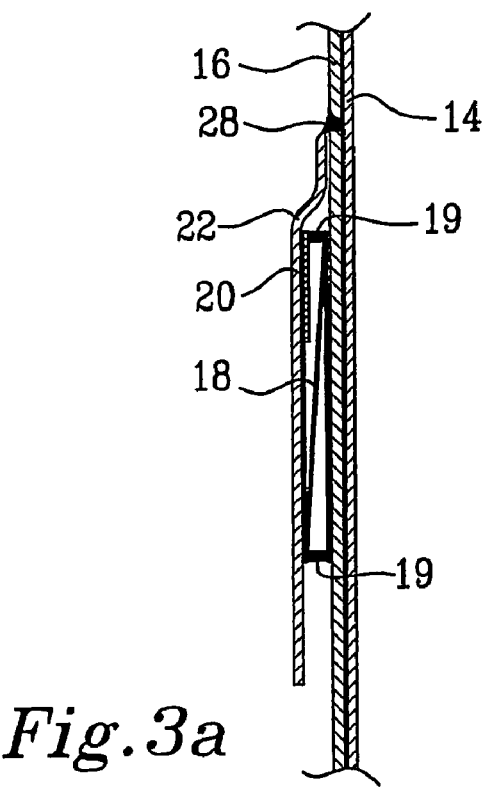
FIG. 3a is a cross-sectional view along the line II-II in FIG. 2.
Figure 3B:
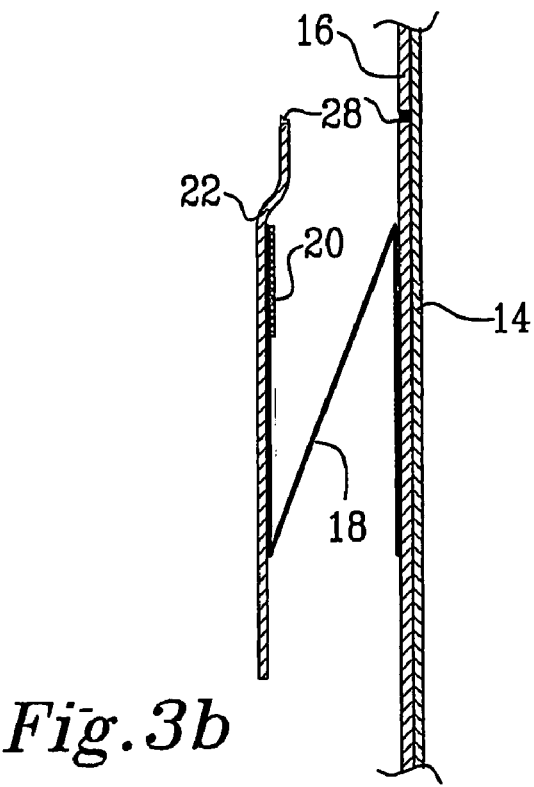
FIG. 3b is a cross-sectional view along the line II-II in FIG. 2 with the disposal fastening means deployed.

FIGS. 3a and 3b are cross-sectional views along the line III-III in FIG. 2. They show the disposal fastening means 18 according to the invention, hidden under the material layer 22. In the embodiment described above, the material layer 22 is not joined to the outer coversheet 16 around part of its periphery (in this case the lower edge) so as to leave place for a finger to be inserted under the material layer 22 and release it from the outer coversheet 16. The disposal fastening means 18 may be of a length such that it must be folded so as to fit under the material layer 22. FIG. 3a shows the disposal fastening means folded in a Z-fold, although other folding forms are conceivable (e.g. C-fold). Distances between components in this figure have been exaggerated for clarity—in the actual product, the components will lie substantially in contact with one another. The disposal fastening means 18 may be held in its folded state by means of suitably-arranged glue sites or welds 19. In contrast to the glue or welds attaching the disposal fastening means 18 to the outer coversheet, the glue or welds 19 holding the folds together will be released when the user or wearer pulls the disposal fastening means 18 by hand.

The glue which holds the disposal fastening means 18 in its folded state may comprise capsules of fragrance which break when the seal is broken. A pleasant smell is thereby released which covers any offensive smells emitted from the absorbent article.

Advantageously, the disposal fastening means 18 is formed from an elastic material, such that—when not under tension—the disposal fastening means 18 lies hidden under the material layer 22 but can be extended under tension.

Figure 4:
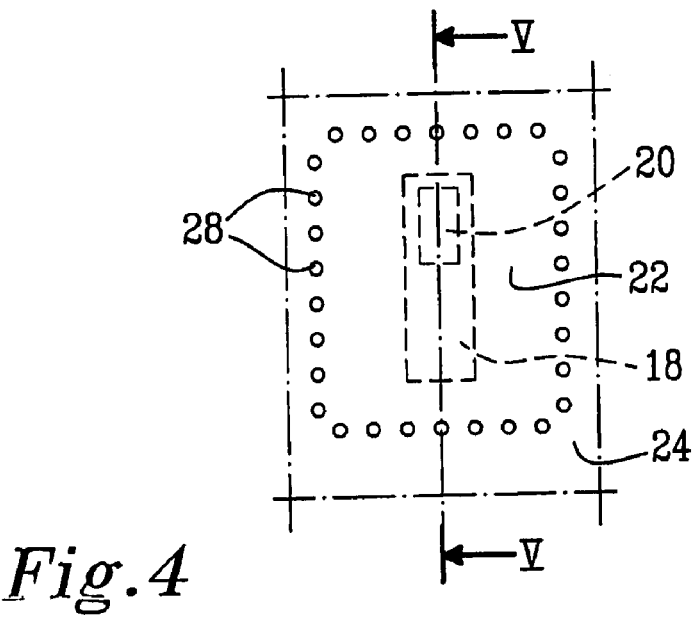
FIG. 4 shows an alternative embodiment of the disposal fastening means according to the invention, in which the material layer is an integral part of the outer coversheet.

In the embodiment shown in FIG. 4 the outer coversheet 16 of the absorbent article 10 is a laminate comprising a garment facing layer 24 and at least one additional layer 26 located on the inside of the garment facing layer. By "inside" is meant the user-facing side of the outer coversheet 16. In this embodiment, the material layer 22 is an integral part of the garment facing layer 24 of the outer coversheet 16.

Figure 5A:
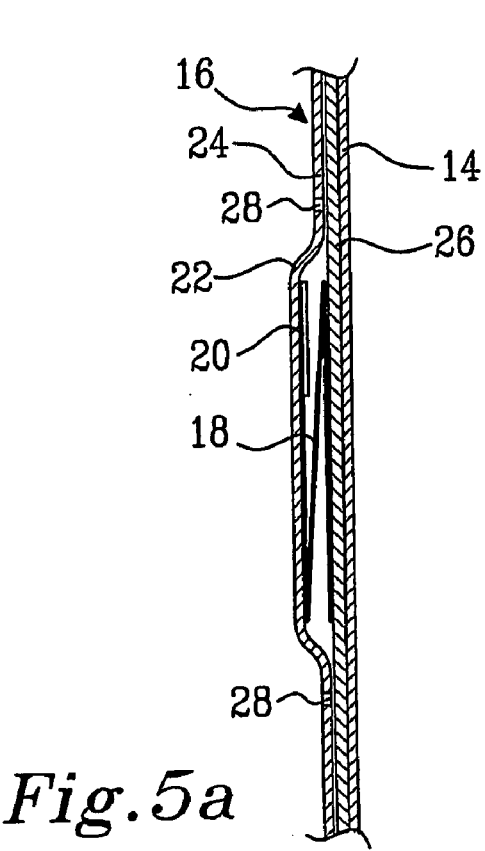
FIG. 5a is a cross-sectional view along the line II-II in FIG. 4.
Figure 5B:
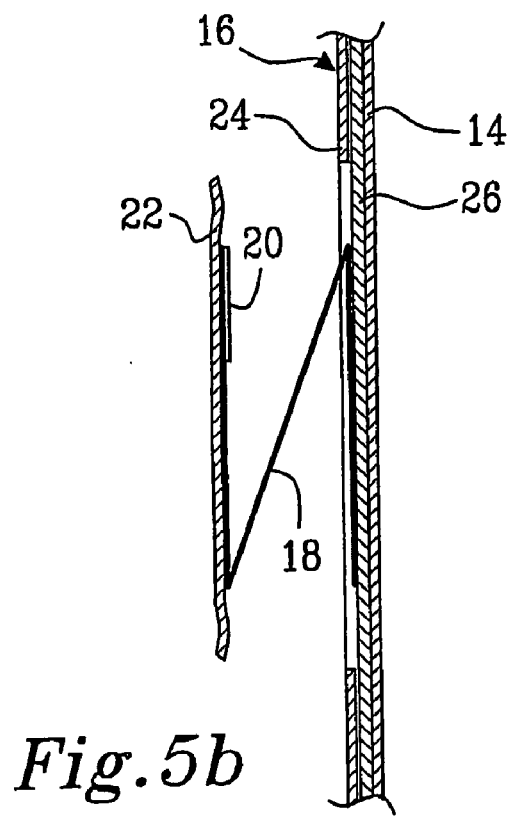
FIG. 5b is a cross-sectional view along the line II-II in FIG. 4 with the disposal fastening means deployed.

FIGS. 5a and 5b are cross-sectional views along the line V-V in FIG. 4. As shown in FIGS. 5a and 5b, the disposal fastening means 18 is located between the garment facing layer 24 of the laminate and the at least one additional layer 26. This embodiment avoids the requirement for a separate material layer 22. Again, distances between components in these figures have been exaggerated for clarity—in the actual product, the components will lie substantially in contact with one another.

To enable a carer or a user to locate and expose the disposal fastening means 18 easily, the garment facing layer 24 of the outer coversheet 16 may be perforated around at least a part of the circumference of the disposal fastening means 18. Removal of the material layer at the perforations 28 exposes the disposal fastening means 18 which is then ready for use.

Again, in this embodiment, the disposal fastening means 18 may or may not be joined to the material layer 22, as appropriate, provided that its function is not hindered.

As mentioned previously, the absorbent article 10 is preferably a pant-type absorbent article. Such pant-type absorbent articles comprise a front portion 30, a crotch portion 32 and a back portion 34, said front and back portions 30, 34 being joined to each other along two opposite longitudinal side edges to define a waist-opening 15 and a pair of leg-openings 17.

The disposal fastening means 18 and associated material layer 22 may be joined to any portion of the outer coversheet 16 of the absorbent article. For ease of access, the disposal fastening means 18 is preferably joined to the front 30 or back 34 portion of the absorbent article rather than in the crotch portion.

Figure 6A:
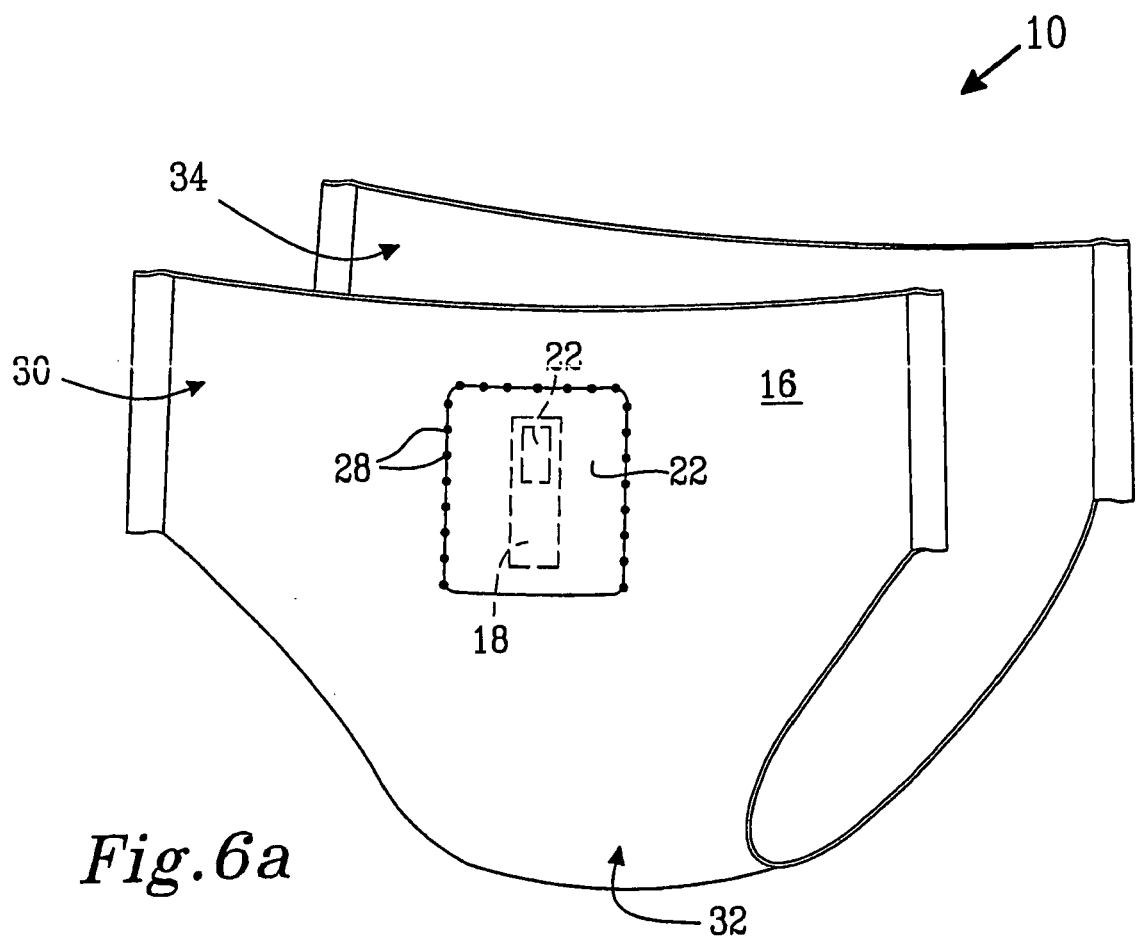
FIGS. 6a-6c illustrate the use of a disposal fastening means according to an embodiment of the invention.
Figure 6B:
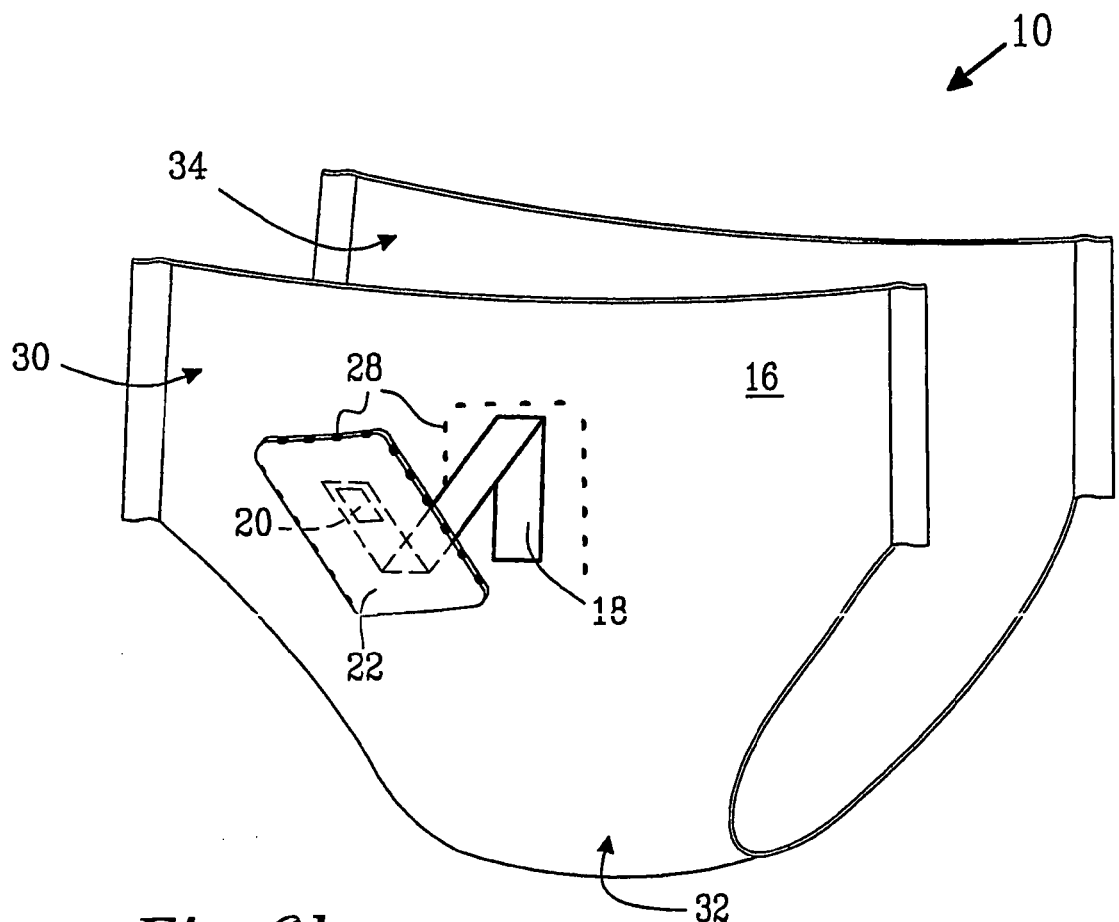
Figure 6C:
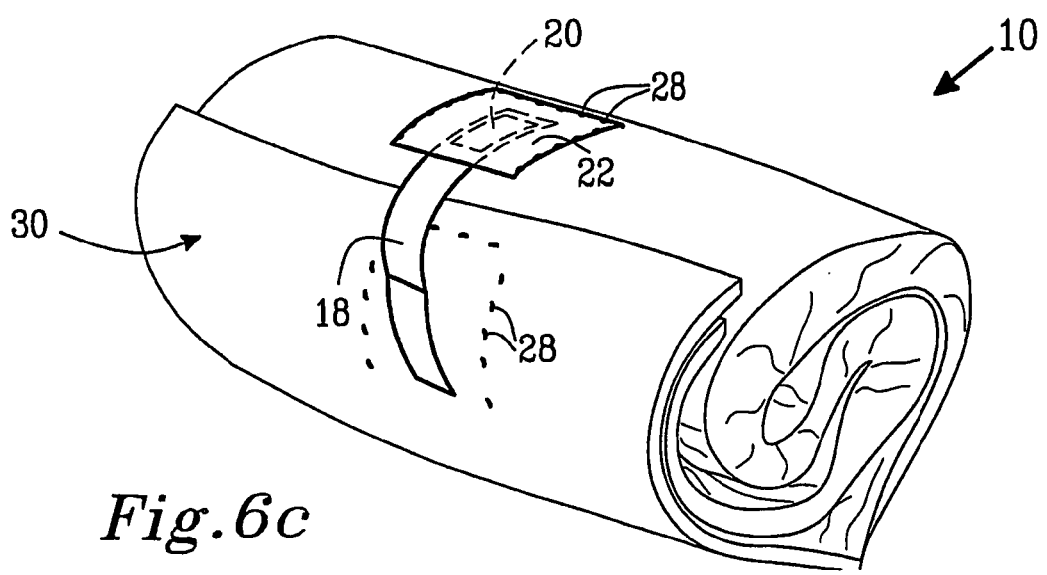

FIGS. 6*a*-*c* illustrate how the disposal fastening means 18 according to the invention is employed when disposing of a soiled diaper. Usually, when a pant-type diaper is removed, the side seams are broken. Then, as shown in FIG. 6*a*, the material layer 22 is removed by tearing perforations or breaking a seal, revealing the disposal fastening means 18. The disposal fastening means 18 is unfolded or stretched out as necessary, as shown in FIG. 6*b*. Finally, the diaper is folded or rolled up into a tight package and the fastening element 20 of the disposal fastening means 18 is affixed to the outer coversheet of the diaper, so as to maintain this folded or rolled up state (FIG. 6*c*). Safe, hygienic disposal of the diaper is thus enabled.

Figure 7A:
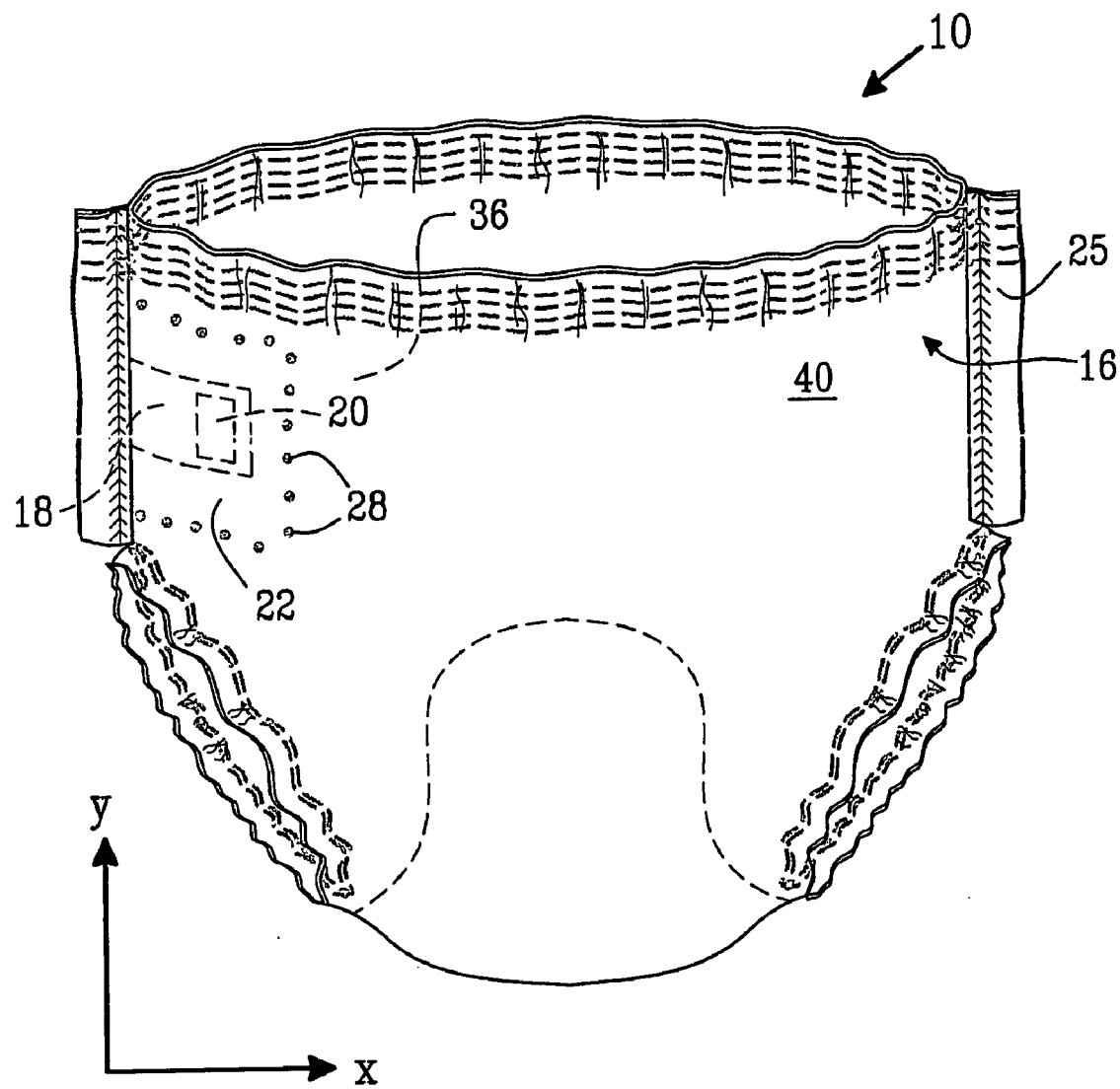
FIGS. 7a-c illustrate how a disposal fastening means according to and embodiment of the invention is incorporated into an absorbent article.
Figure 7B:
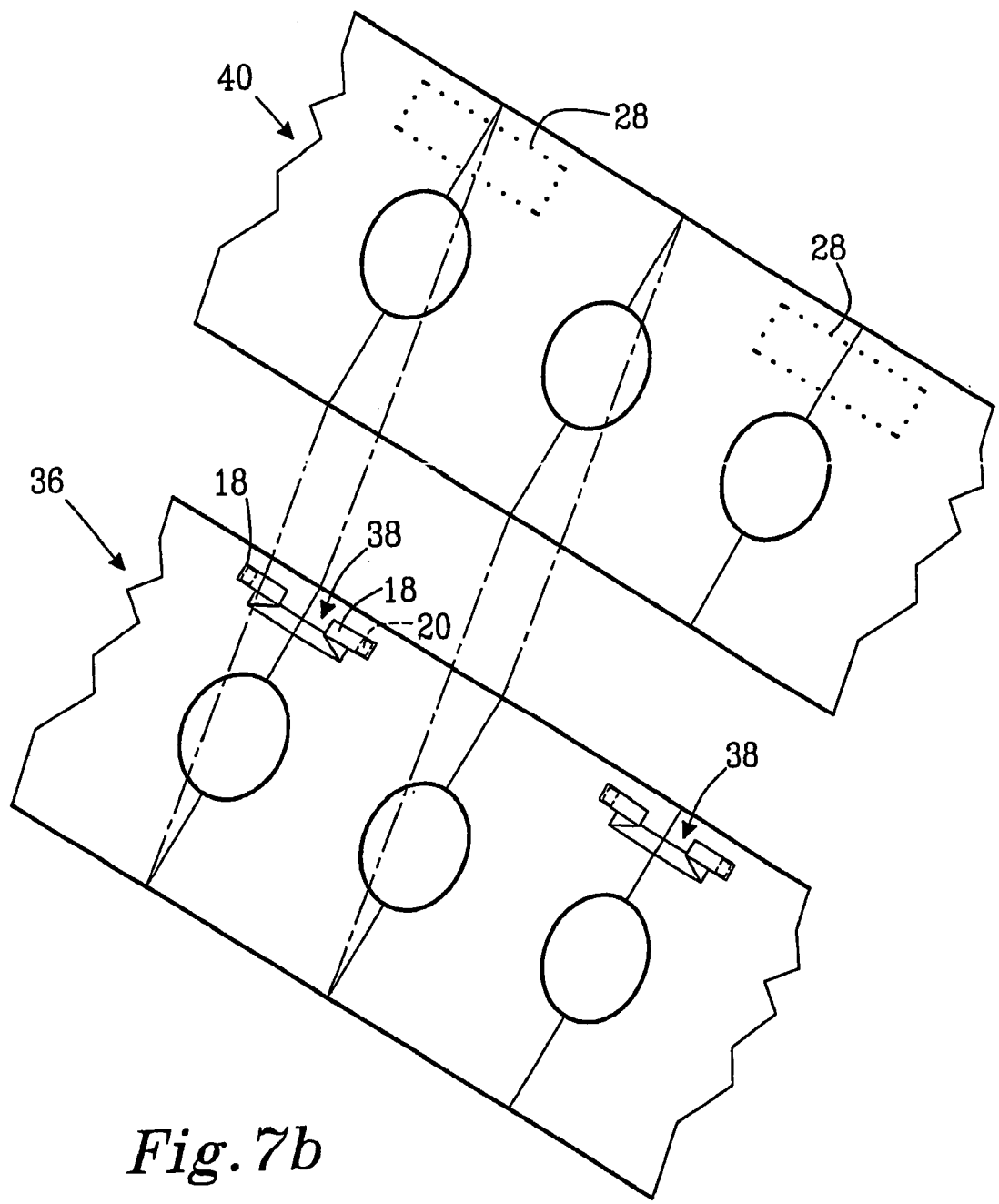
Figure 7C:
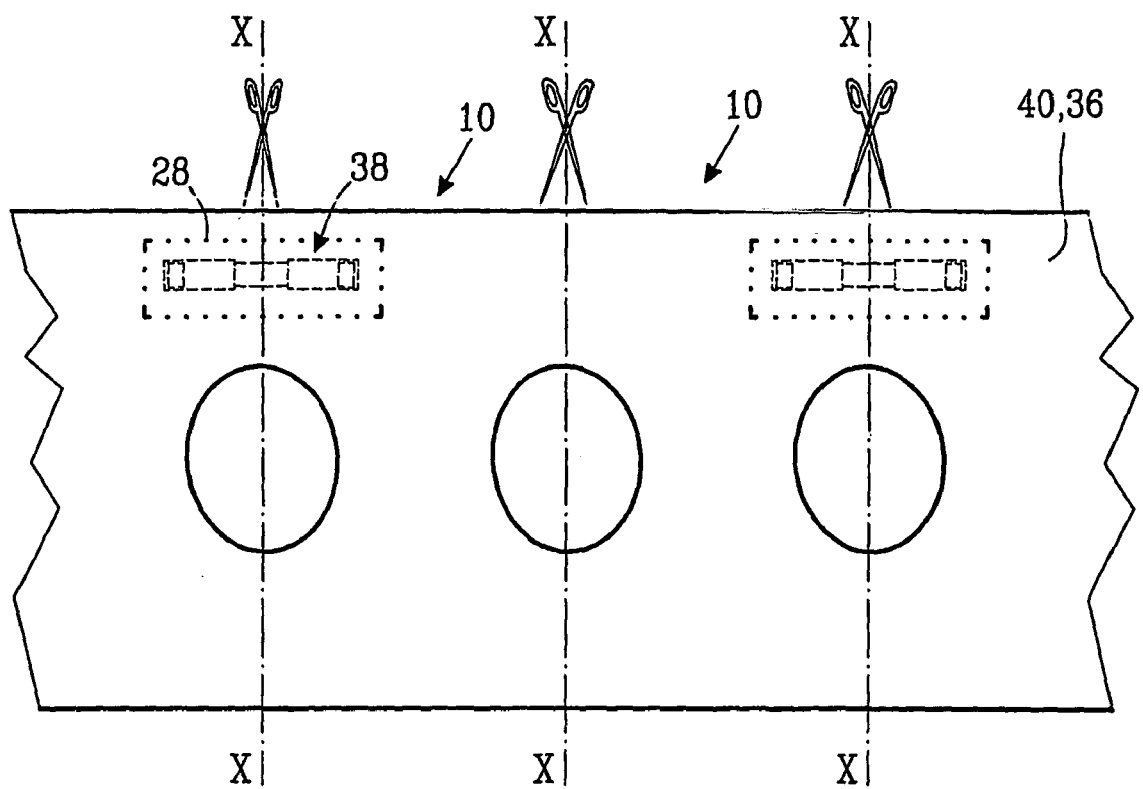

FIG. 7*a* shows a pant diaper containing the disposal fastening means 18 according to the present invention in which the disposal fastening means is close to the side seams 25 of the article and in which it is located between the garment facing layer 24 of the laminate and the at least one additional layer 26. FIGS. 7*b* and 7*c* show the construction of such an article.

In this case, the garment-facing layer 24 of the laminate is a nonwoven layer 40 and the additional layer is a plastic film 36. During manufacture, a double Z-folded strip 38 is attached to a web of the plastic film 36 in the area which is to become the side seams 25 such that it overlaps the joint between two adjacent articles on the web of plastic film as shown in FIG. 7*b*. The double Z-folded strip 38 comprises fastening element 20 at each end, and may be maintained in its Z-folded form by weak welds or glue sites 19.

A web of nonwoven material 40 is affixed on top of the first web of plastic film 36. The webs are not attached to each other in the area around the double Z-folded strip 38. The second web of material 40 may comprise perforations 28 marking the position of the double Z-folded strip 38. The double Z-folded strip 38 is therefore located between the plastic film 36 and the nonwoven material 40. Once joined, the absorbent articles are separated from one another by cutting through both webs and the double Z-folded strip 38 along the line X-X shown in FIG. 7*c*, which passes through the midpoint of the double Z-folded strip 38. The cutting process produces an edge between two articles, each of which incorporates a disposal fastening means 18 in the area around the side seam 25.

Extra components such as inner coversheets, absorbent cores, elastic threads or material at the waist or leg openings or leakage barriers for the leg/waist openings may be included in the manufacturing process as required. Waistband material may be joined to each edge of the articles as required. The diapers are folded in half to form a pant-like shape, and the edges containing the disposal fastening means 18 are bonded to each other to form side-seams.

The invention is not limited to the embodiments described above and shown in the drawings, but may be varied within the scope of the claims, and equivalents thereof. In particular, the invention is not limited to a particular type of absorbent article, but the embodiments shown may be applied to any type of absorbent article. Details from the different embodiments may of course be combined as desired, as will be evident to the person skilled in the art.

The invention claimed is:

1. An absorbent article comprising:
an inner coversheet, an outer coversheet, an absorbent core disposed between the inner coversheet and the outer coversheet; and
at least one disposal fastener which is directly or indirectly joined to the outer coversheet, the disposal fastener comprising a fastening element adapted to fasten to at least a portion of the outer coversheet, which allows the article to be secured in a configuration that provides a convenient disposal after the article has been used, the article having a longitudinal and a transverse direction;
wherein the disposal fastener is covered by a material layer having a surface area such that the material layer extends beyond the disposal fastener in every direction, the material layer being attached to or forming an integral part of the outer coversheet to keep the disposal fastener hidden when not in use, and the material layer is releasable from the outer coversheet to expose the disposal fastener for use.

2. An absorbent article comprising:
an inner coversheet, an outer coversheet, an absorbent core disposed between the inner coversheet and the outer coversheet; and
at least one disposal fastener which is directly or indirectly joined to the outer coversheet, the disposal fastener comprising a fastening element adapted to fasten to at least a portion of the outer coversheet, which allows the article to be secured in a configuration that provides a convenient disposal after the article has been used, the article having a longitudinal and a transverse direction;
wherein the disposal fastener is covered by a material layer having a surface area such that the material layer extends beyond the disposal fastener in every direction, the material layer being attached to or forming an integral part of the outer coversheet to keep the disposal fastener hidden when not in use, and the material layer is releasable from the outer coversheet to expose the disposal fastener for use; and
wherein the material layer is provided with perforations or breakable seals for releasing the material layer from the outer coversheet and thus exposing the disposal fastener.

3. The absorbent article according to claim 1, wherein the outer coversheet is a laminate comprising a garment facing layer and at least one additional layer located on the inside of the garment facing layer.

4. The absorbent article according to claim 3, wherein the material layer is an integral part of the garment facing layer of the outer coversheet.

5. The absorbent article according to claim 3, wherein the garment facing layer is perforated around at least a part of the circumference of the material layer.

6. The absorbent article according to claim 1 wherein the material layer is a separate piece of material which is joined to the outer coversheet by a breakable seal.

7. The absorbent article according to claim 6, wherein the breakable seal comprises welds or glue sites which join the material layer to the outer coversheet.

8. The absorbent article according to claim 1, wherein the material layer is of a composition and structure such that the material layer closely resembles the garment-facing surface of the outer coversheet.

9. The absorbent article according to claim 1, wherein the outer coversheet comprises nonwoven material in at least the garment-facing surface thereof.

10. The absorbent article according to claim 1, wherein the fastening element is a hook portion of a hook-and-loop type fastener.

11. The absorbent article according to claim 1, wherein the fastening element is an adhesive tape tab.

12. The absorbent article according to claim 1, wherein the disposal fastener is folded under the material layer.

13. The absorbent article according to claim 1, wherein the disposal fastener is joined to the material layer.

14. The absorbent article according to claim 1, wherein the material layer is an integral part of the outer surface of the disposal fastener.

15. The absorbent article according to claim 1, wherein the disposal fastener comprises an elastic material such that, when not under tension, the disposal fastener lies hidden under the material layer but can be extended under tension.

16. The absorbent article according to claim 1, wherein the article is a pant-type absorbent article comprising a front portion, a crotch portion and a back portion, said front and back portions being joined to each other along two opposite longitudinal side edges to define a waist-opening and a pair of leg-openings.

17. The absorbent article according to claim 16, wherein the disposal fastener is located on the front or back portion of the article.

18. The absorbent article according to claim 1, wherein a pattern is printed on a garment-facing surface of the outer coversheet and at least a part of said pattern is located on the material layer.

19. The absorbent article according to claim 1, wherein the absorbent article is one of a diaper, a pant diaper, a sanitary napkin, and an incontinence guard.

20. The absorbent article according to claim 8, wherein the material layer is a nonwoven material.

21. The absorbent article according to claim 8, wherein the material layer is a plastic film.

22. The absorbent article according to claim 1, wherein the disposal fastener is made from an elastic material.

23. An absorbent article comprising:
an inner coversheet, an outer coversheet, an absorbent core disposed between the inner coversheet and the outer coversheet; and
at least one disposal fastener which is directly or indirectly joined to the outer coversheet, the disposal fastener comprising a fastening element adapted to fasten to at least a portion of the outer coversheet, which allows the article to be secured in a configuration that provides a convenient disposal after the article has been used, the article having a longitudinal and a transverse direction;
wherein the disposal fastener is covered by a material layer having a surface area such that the material layer extends beyond the disposal fastener in every direction, the material layer being fixed to the disposal fastener and being attached to or forming an integral part of the outer coversheet to keep the disposal fastener hidden when not in use, and the material layer is releasable from the outer coversheet to expose the disposal fastener for use.

24. The absorbent article according to claim 1, wherein the material layer keeps the disposal fastener completely hidden when the disposal fastener is not in use.

25. An absorbent article comprising:
an inner coversheet, an outer coversheet, an absorbent core disposed between the inner coversheet and the outer coversheet; and
at least one disposal fastener which is directly or indirectly joined to the outer coversheet, the disposal fastener comprising a fastening element adapted to fasten to at least a portion of the outer coversheet, which allows the article to be secured in a configuration that provides a convenient disposal after the article has been used, the article having a longitudinal and a transverse direction;
wherein the disposal fastener is covered by a material layer having a surface area such that the material layer extends beyond the disposal fastener in every direction, the material layer being detachably attached to or forming a detachable integral part of the outer coversheet to keep the disposal fastener hidden when not in use, and the material layer is configured to be removed from the outer coversheet to expose and utilize the disposal fastener.

* * * * *